United States Patent
Kim et al.

(10) Patent No.: US 10,603,207 B2
(45) Date of Patent: Mar. 31, 2020

(54) MANDIBULAR ADVANCEMENT DEVICE WITH GUIDE CHANNEL

(71) Applicant: ProSomnus Sleep Technologies, Inc., Pleasanton, CA (US)

(72) Inventors: Sung Kim, Pleasanton, CA (US); David W. Kuhns, Pleasanton, CA (US); Leonard A. Liptak, Pleasanton, CA (US)

(73) Assignee: PROSOMNUS SLEEP TECHNOLOGIES, INC., Pleasanton, CA (US)

(*) Notice: Subject to any disclaimer, the term of this patent is extended or adjusted under 35 U.S.C. 154(b) by 382 days.

(21) Appl. No.: 15/727,508

(22) Filed: Oct. 6, 2017

(65) Prior Publication Data

US 2019/0015246 A1 Jan. 17, 2019

Related U.S. Application Data

(60) Provisional application No. 62/533,420, filed on Jul. 17, 2017.

(51) Int. Cl.
*A61F 5/56* (2006.01)

(52) U.S. Cl.
CPC .................................. *A61F 5/566* (2013.01)

(58) Field of Classification Search
CPC ............ A63B 2071/086; A63B 71/085; A61B 2071/086; A61F 5/56; A61F 5/566; A61C 7/08; A61C 7/36

USPC .... 128/848, 859–862, 869; 433/6–7, 72–76; 602/902

See application file for complete search history.

(56) References Cited

U.S. PATENT DOCUMENTS

| | | | | |
|---|---|---|---|---|
| 6,055,986 | A * | 5/2000 | Meade | 128/848 |
| 8,517,029 | B2 * | 8/2013 | Nelissen | 128/848 |
| 8,646,454 | B1 | 2/2014 | Moses et al. | |
| 2011/0017220 | A1 * | 1/2011 | Lindsay | 128/848 |
| 2012/0227750 | A1 * | 9/2012 | Tucker | 128/848 |
| 2013/0269712 | A1 | 10/2013 | Awde | |

FOREIGN PATENT DOCUMENTS

| KR | 20130029183 A | 3/2013 |
|---|---|---|
| KR | 101654279 B1 | 9/2016 |

OTHER PUBLICATIONS

International Search Report and Written Opinion issued in PCT/US2018/042334 dated Sep. 13, 2018 (8 pages).

* cited by examiner

*Primary Examiner* — Anna K Kinsaul
*Assistant Examiner* — Trisha Talapatra
(74) *Attorney, Agent, or Firm* — Tahmassebi IP Law Group, P.C.; Sam K. Tahmassebi

(57) ABSTRACT

Disclosed herein are splints for a mandibular advancement device, each splint comprising one or more guided fins, wherein each guided fin is located at a distance D from back of the splint; a back post; at least one threaded rod connecting the back post to the guided fin, wherein the distance between the guided fin and the back post is changed when the threaded rod is turned either clockwise or counterclockwise; and a guiding mechanism.

11 Claims, 6 Drawing Sheets

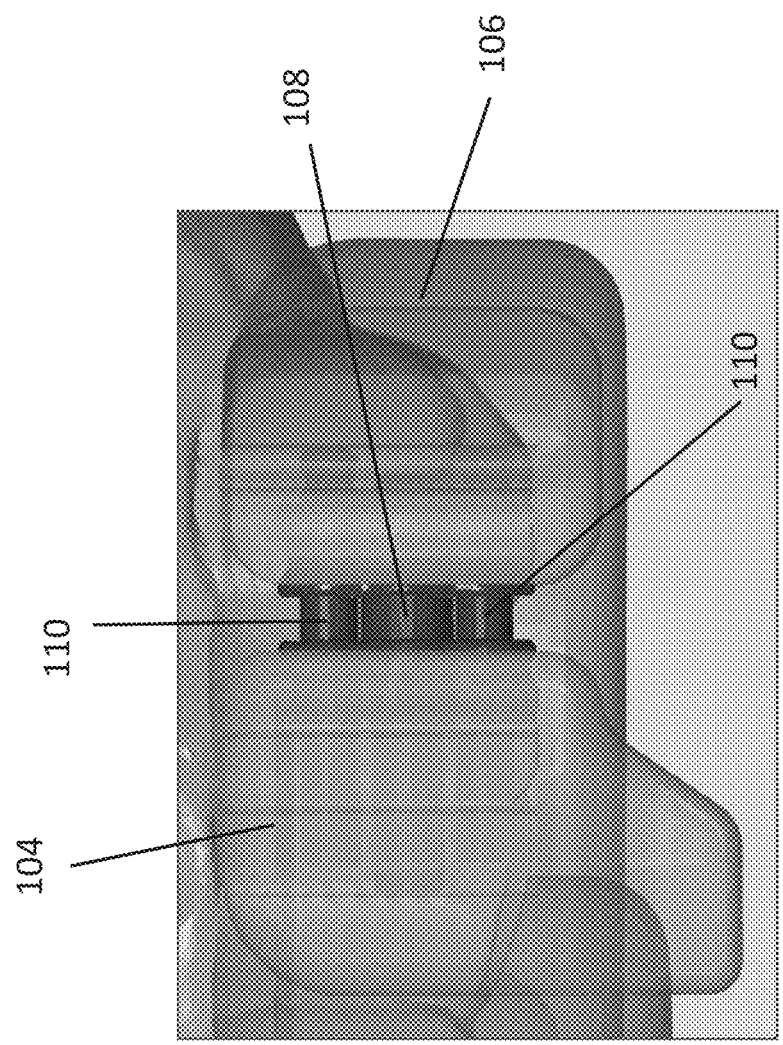

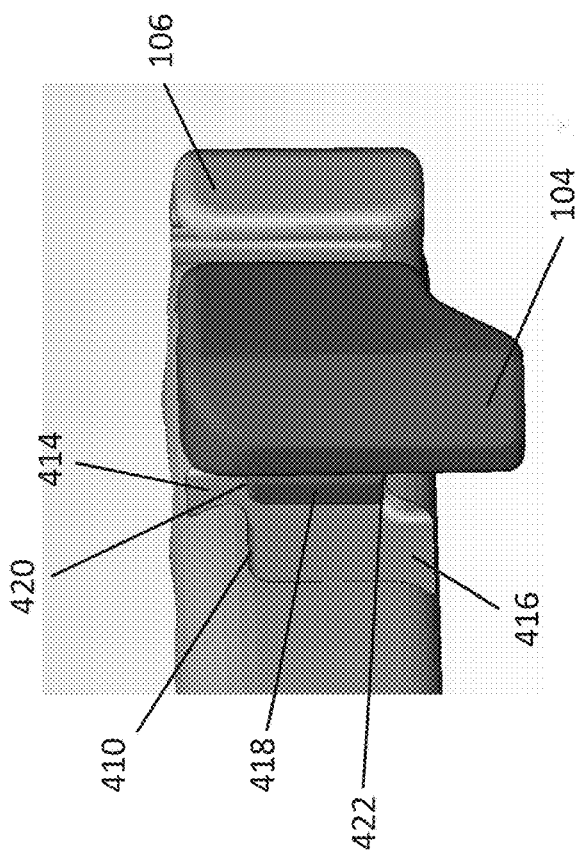
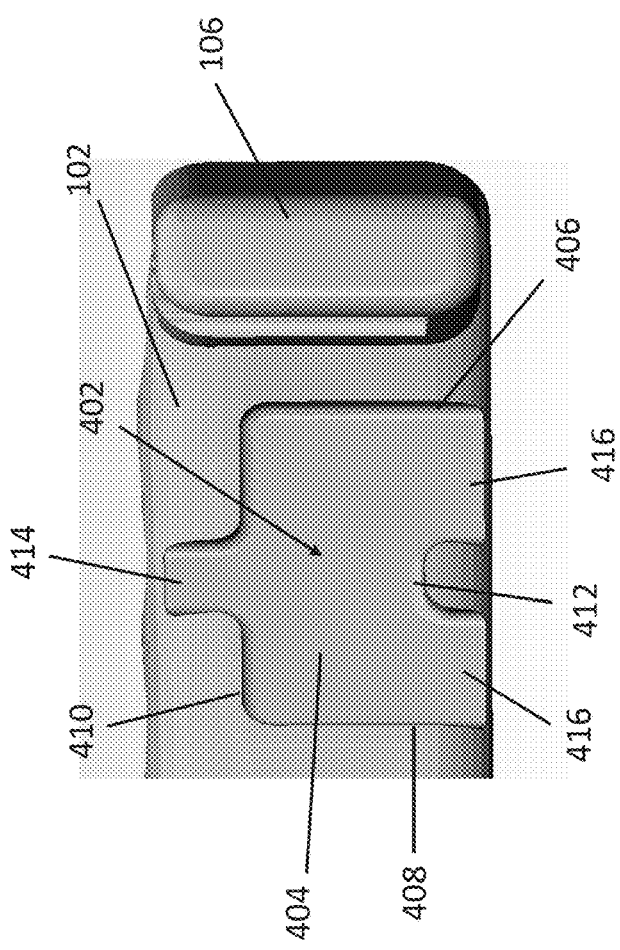
Figure 4B
Figure 4A

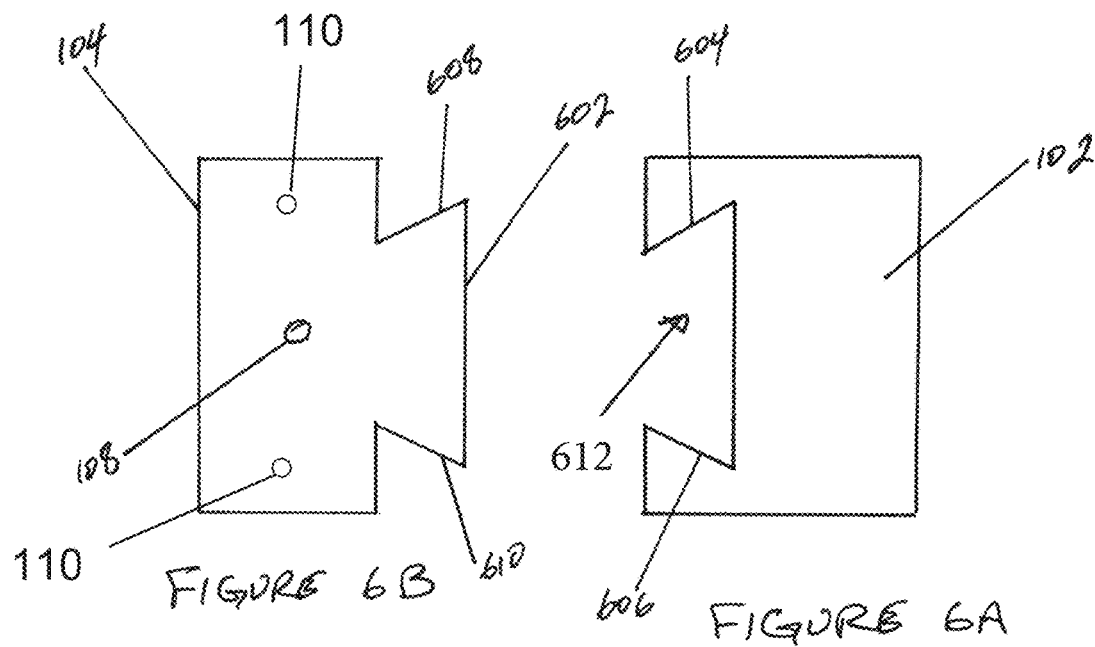
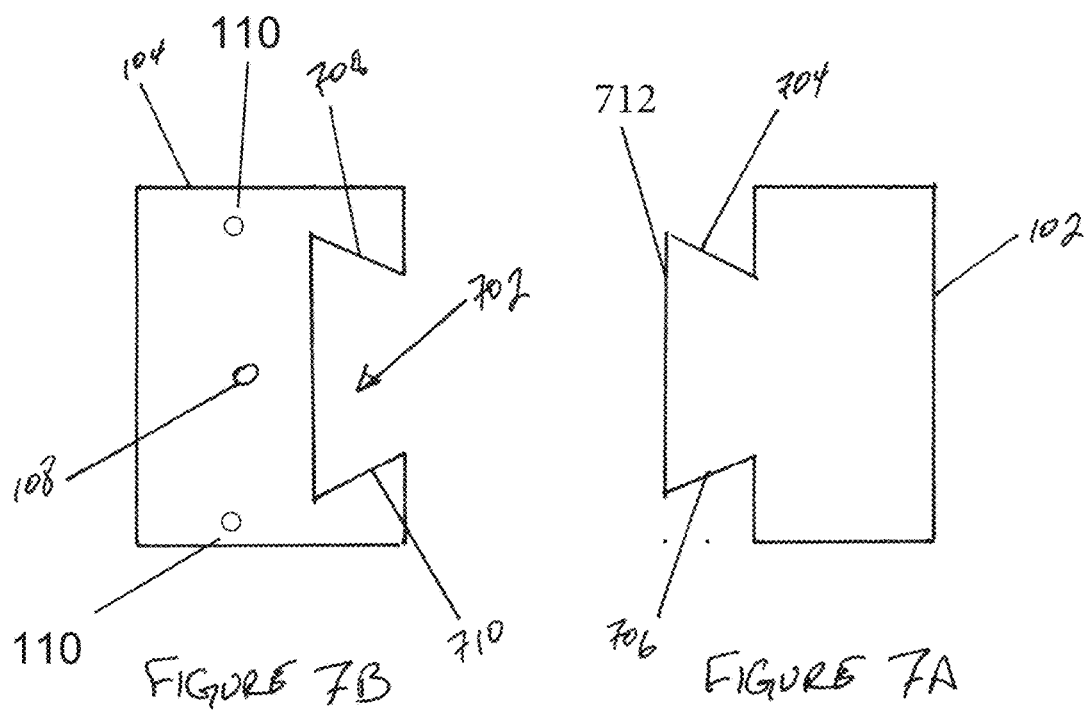

MANDIBULAR ADVANCEMENT DEVICE WITH GUIDE CHANNEL

RELATED APPLICATIONS

The present application claims priority to the U.S. Provisional Application Ser. No. 62/533,420, filed on Jul. 17, 2017, by KIM et al., and entitled "MANDIBULAR ADVANCEMENT DEVICE WITH GUIDE CHANNEL," the entire disclosure of which is incorporated by reference herein, including the drawings.

FIELD OF THE INVENTION

The present invention is in the field of medical devices, and in particular it is in the field of mandibular advancement devices.

BACKGROUND OF THE DISCLOSURE

Snoring and mild sleep apnea are generally thought to be the result of a reduced or partial constriction of the airway during sleep. This may be attributed to soft tissue sinking and applying pressure on the airway during sleep including the mandible dropping and moving backwards. Mandibular advancement devices (MADs) are designed to move the mandible forward to relieve the force applied from soft tissue during sleep and assisting in opening the airway. Depending on the patient, the advancement of the mandible may vary based on the response of the patient. Optimizing the adjustment is referred to as titration.

The present applicant has disclosed several embodiments of MADs in previous publications, which include: U.S. application Ser. Nos. 14/809,208, 15/416,666, 15/416,715, and International Application No. PCT/US2017/015530, the disclosure of all of which is incorporated by reference herein, including the drawings. In some applications, it is necessary to have a finer adjustment of mandibular advancement that is possible using the MADs disclosed in the above-incorporated publications. Accordingly, a need exists in the art to modify the design of the above-referenced MADs to allow for fine adjustments.

SUMMARY OF THE INVENTION

Disclosed herein are splints for a mandibular advancement device, each splint comprising one or more guided fins, wherein each guided fin is located at a distance D from back of the splint; a back post; at least one threaded rod connecting the back post to the guided fin, wherein the distance between the guided fin and the back post is changed when the threaded rod is turned either clockwise or counterclockwise; and a guiding mechanism.

BRIEF DESCRIPTION OF THE DRAWINGS

FIG. 3 is a close-up drawing of the side view of one embodiment of the adjustable fin of the disclosed MADs.

FIG. 4A is a drawing of one embodiment of the adjustable fin location.

FIG. 4B is a drawing showing a fin placed in the embodiment of the adjustable fin location of FIG. 4A.

FIG. 6A is one embodiment of the cross-section view of the embodiment of the channel of FIG. 5, cut along the A-A line. FIG. 6B shows the cross section of a guided fin that fits in the embodiment of FIG. 6A.

FIG. 7A is one embodiment of the cross-section view of the embodiment of the channel of FIG. 5, cut along the A-A line. FIG. 7B shows the cross section of a guided fin that fits in the embodiment of FIG. 7A.

DETAILED DESCRIPTION OF THE EMBODIMENTS

Figure 1:
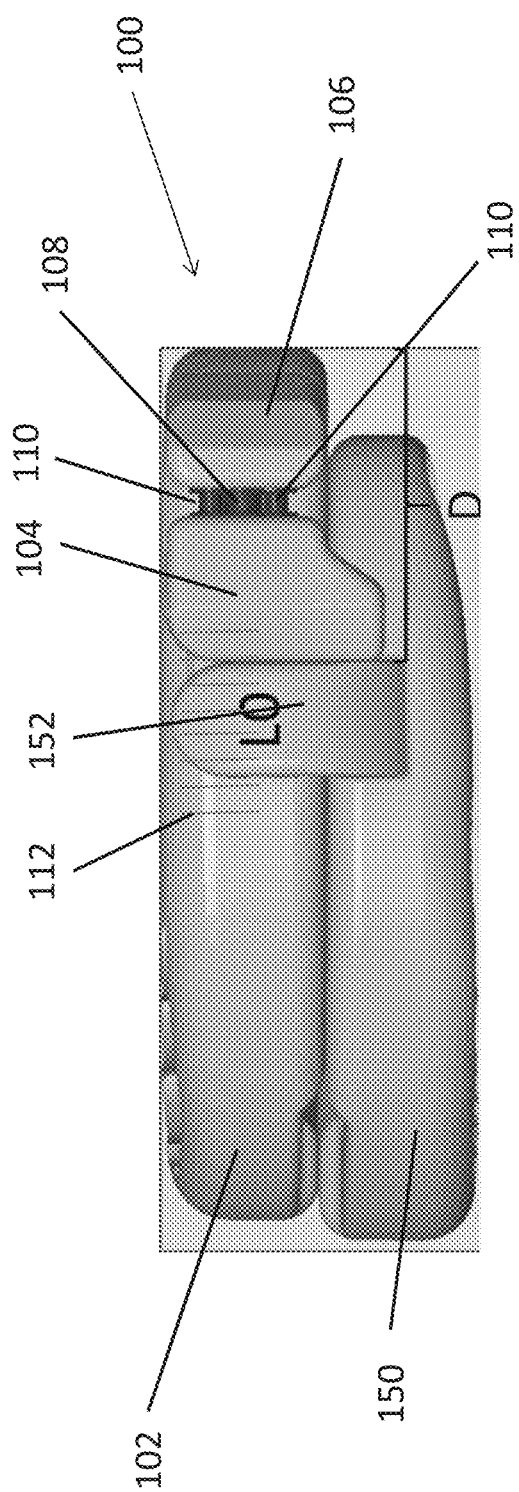
FIG. 1 is a drawing of the side view of one embodiment of the disclosed MADs having a guided fin location, and showing the disclosed fiducial marks.

Disclosed herein are improvements to the mandibular advancement devices (MADs) disclosed in U.S. Patent Application Publication Nos. 2016/0184129 and 2017/0143537, U.S. application Ser. No. 15/416,715, and International Publication No. WO 2017/132638. The foregoing applications are incorporated by reference herein in their entirety, including the drawings.

Both the upper and lower splints of the previously described MADs feature fins that are immobile. A proper mandibular advancement is obtained by titrating the patient. The previously described methods included steps in which different combinations of upper and lower splints, each having fins affixed in slightly different distance from the back of the splint, are used to find the most effective mandibular advancement. See, for example, the above-incorporated references.

In one aspect, the present disclosure is directed to MADs and methods of their use, where one of the upper or lower splints comprises a guided fin. Using the presently disclosed MADs, one splint (either upper or lower) having a guided fin is used in conjunction with a set of opposing splints having varying fin positions. This combination allows for a wider range of advancement distances using fewer splints, as compared with the previously disclosed systems.

In another aspect, the present disclosure is directed to MADs and methods of manufacturing thereof, whether the MADS are the ones disclosed herein or in the above-incorporated publications, by incorporating into the design of the splint at least one anchor point for the future attachment of an accessory.

Thus, in the first aspect, disclosed herein are splints 102 for a mandibular advancement device 100, the splint 102 comprising:

an imprint of the patient's dentition along a plane of the splint 102 contacting the dentition;

one or more fins 104, wherein each fin 104 is located at a distance D from back of the splint 102;

each fin 104 is "L" shaped, with the leg of the "L" connecting the fin 104 to its respective splint 102 protruding along the occlusal plane buccally, while the other leg of the "L" protruding perpendicular to the occlusal plane away from the patient's gingiva;

a back post 106, wherein the back post 106 protrudes along the occlusal plane buccally to about the same extent as the fin 104;

at least one threaded rod 108 connecting the back post 106 to the fin 104, wherein the distance between the fin 104 and the back post 106 is changed when the threaded rod 108 is turned either clockwise or counterclockwise; and a guiding mechanism.

In some embodiments, the splint is arch-shaped.

The guiding mechanism connects a fin to the splint. The fin with the guiding mechanism is referred to herein as the "guided fin." The guiding mechanism provides a guided path along which the guided fin travels as the distance between the guided fin and the back post is changed. Certain products currently on the market feature a fin connected to a back post, where the distance between the fin and the back post can be changed by turning a screw. However, in these products, the fin is not guided.

An unguided fin travels in a straight line. However, the splint is arched and slightly curved. Therefore, when the fin is extended anteriorly, an increasing gap between the fin and the splint develops, which can cause patient discomfort. The gap further turns the fin into a lever with the fulcrum being the back post. As the distance between the fin and the back post increases, the effort by the cheeks on the anterior end of the fin becomes sufficient to break or damage the mechanism. Further, in the current designs, anterior extension of the fin is linear, whereas the distance between the upper fin and the lower fin is arced. Thus, when the patient adjusts the fin location to a certain degree, the actual adjustment is different because the linear displacement of the fin is not translated to the curved path of the splint. Therefore, the actual extent of mandibular advancement will be somewhat less than what the patient intended. The uncertainty caused by the differences between the curved and linear paths introduce a large error into the extent of mandibular advancement that defeats the treatment goals.

In some embodiments, the splint having the guiding mechanism and the guided fin is an upper splint, whereas in other embodiments, the splint is a lower splint.

Referring now to the drawings, embodiments of the MADs disclosed herein are described.

FIG. 1 depicts an embodiment of a mandibular advancement device 100 having a splint 102 with the guided fin 104 as disclosed herein. FIG. 1 also shows a lower splint 150 having a stationary fin 152. The lower splint 150 is shown here to illustrate the engagement of the upper and lower splints.

The splint 102 comprises one or more guided fins 104. In some embodiments, the splint 102 comprises two guided fins 104, one at each posterior end of the splint arch. The anterior face of each guided fin 104 is located at a distance D from the posterior-most end of the splint 102, as shown in FIG. 1. As is discussed below, the distance D is adjustable.

The splint 102 further comprises a back post 106. In some embodiments, the location of the back post 106 on the splint 102 is not changeable. The back post 106 provides the anchor for the guided fin.

In some embodiments, the back post 106 protrudes along the occlusal plane buccally to about the same extent as the guided fin 104. In other words, as clearly seen in FIGS. 2A & 2B, the buccal surface of the guided fin 104 is flush, or nearly flush, with the buccal surface of the back post 106. While this feature is not necessary for the proper function of the MAD, it provides additional patient comfort by presenting a seemingly flat surface for the combination of fin and back post.

As shown more clearly in FIG. 3, in some embodiments, at least one threaded rod 108 connects the back post 106 to the guided fin 104. In these embodiments, there is a corresponding threaded hole (akin to a nut) in the guided fin 104. The threaded rod 108 itself is not displaced with respect to the back post 106. Instead, rotating the threaded rod 108 causes the guided fin 104 to move further or closer to the back post 106, depending on the direction of the turn. In some embodiments, turning the threaded rod 108 clockwise causes the guided fin 104 to move away from the back post 106, while turning the threaded rod 108 counterclockwise causes the guided fin 104 to move towards from the back post 106. And vice versa.

Figure 2A:
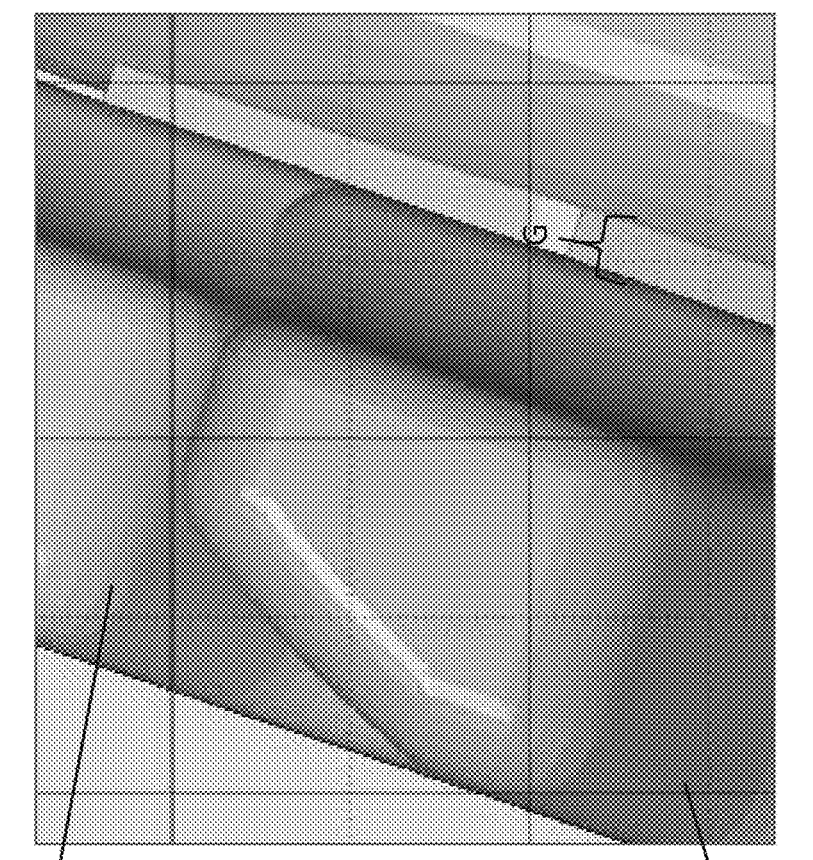
FIG. 2A is a drawing of the top view of the posterior portion of one side of one embodiment of the disclosed MADs having a guided fin location.
Figure 2B:
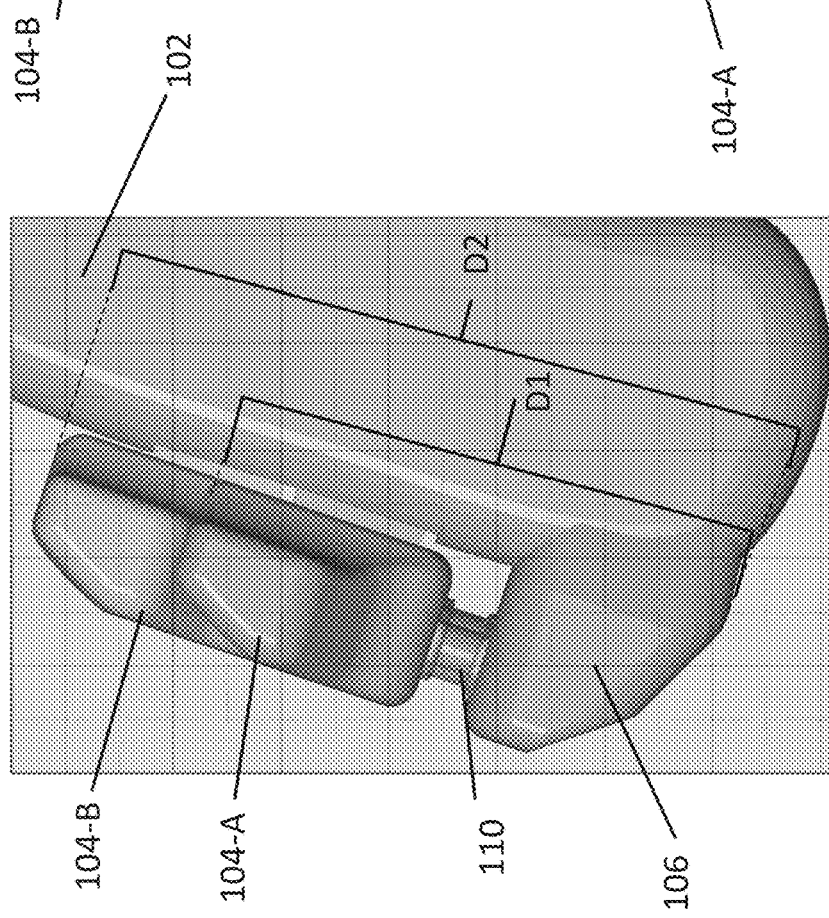
FIG. 2B is a close up view of the gap between the disclosed guided fin and the splint to which it is attached.

As mentioned above, the guiding mechanism serves a number of purposes. First, the guiding mechanism guides the moving fin along a path that follows the curvature of the splint to which the fin is connected. FIGS. 2A & 2B depict the relative position of the guided fin 104 with respect to the splint 102 as the guided fin 104 changes positions anteriorly. FIG. 2B is a close up view of the guided fin 104 begins at a posterior position 104A, where the anterior edge of the guided fin 104 is at a distance D1 from the posterior-most edge of the back post 106. After the threading is complete, the guided fin 104 rests at an anterior position 104B, where the anterior edge of the guided fin 104 is now at a distance D2 from the posterior-most edge of the back post 106, where D2>D1. However, regardless of the curvature of the splint 102, the gap G (FIG. 2B) between the guided fin 104 and the splint 102 at position 104A is substantially the same width as the gap G at position 104B. In other words, the guided fin 104 does not extend buccally away from the splint 102 as the guided fin 104 is moved anteriorly. Keeping the gap G constant keeps the torque on the stabilizing rods 110 (see below) constant and reduces the chance that the either the guided fin 104 or the back post 106 would break during use.

In addition, by keeping the gap G constant regardless of the position of the guided fin 104, the patient's sensation of the appliance in their mouth does not change significantly when the guided fin 104 is moved. This reduces the level of patient discomfort as the fin position is changed and the patient does not need to get used to the new position. Consequently, the quality of the patient's sleep remains the same as before the change was made.

Further, the guiding mechanism comprises a positive stop at the anterior end of the guiding mechanism that prevents the guided fin 104 from being threaded too far and become separated from the back post 106.

As shown in FIG. 3, in some embodiments, the guiding mechanism further comprises at least one stabilizing rod 110 connecting the back post 106 to the guided fin 104. The stabilizing rod 110 provides support for the guided fin 104. In some embodiments, the stabilizing rod 110 is affixed to the back post 106. In these embodiments, the stabilizing rod 110 does not move as the guided fin 104 moves away or towards the back post 106. In these embodiments, the guided fin 104 glides over the stabilizing rod 110. In other embodiments, the stabilizing rod 110 is affixed to, and moves along with, the guided fin 104. The embodiment shown in FIG. 3 comprises two stabilizing rods 110 one at each side of the threaded rod 108.

In some embodiments, a guiding mechanism guides the path of the guided fin 104 along the arch of the splint 102. FIGS. 4A & 4B show an embodiment of a guiding channel 402. In some embodiments, the guiding channel 402 is an indentation in the body of the splint 102. The guiding channel 402 comprises a substantially rectangular core section 404. The core 404 is at least partially bound on all sides by a short wall. The short wall is created when the guiding channel 402 is indented into the splint 102.

In some embodiments, the position of the guiding channel 402 on the splint 102 is dictated by the individual idiosyncrasies of the patient's oral anatomy. In some of these embodiments, a physician or dentist who examines and orders the splint for the patient determines where the guiding channel should be located on the splint and gives the coordinates of the guiding channel in the x,y,z plane to the manufacturer of the splint. The 3-dimensional positioning of the guiding channel affects the path of the guiding mechanism as its position is changed to move the mandible forward. A 1 mm forward movement of the guiding mechanism does not necessarily translate to a 1 mm advancement of the mandible due to the curved path and the position of the guiding channel. The health care professional, e.g., doctor or dentist, can take the 3-dimensional position of the guiding mechanism into account when providing the prescription for the device or its use. Accordingly, the x,y,z position of the guiding channel is not arbitrary. Thus, in these embodiments, the guiding channel is placed according to a prescription by the health care provider.

The posterior wall 406 acts as a backstop for the guided fin 104. When the guided fin 104 is threaded posteriorly, it stops at the posterior wall 406 and cannot move any further back. The posterior wall 406, therefore, determines the posterior-most point for the guided fin 104. In some embodiments, the posterior wall 406 is flush with, or is the anterior surface of, the back post 106.

The anterior wall 408 forms an anterior positive stop for the guided fin 104. When the guided fin 104 is threaded anteriorly, it cannot get past the anterior wall 408. Consequently, the anterior wall 408 determines the anterior-most point for the guided fin 104. The anterior wall 408 prevents the guided fin 104 from being threaded so far that it becomes disconnected from the threaded rod 108.

The superior wall 410 and the inferior wall 412 prevent the up-down movement of the guided fin 104 (i.e., movement within the patient's sagittal plane) and force it to travel parallel to the splint 102 as it moves parallel to the anteroposterior axis in the anterior-posterior direction.

In the embodiment shown in FIG. 4A, the guiding mechanism 402 is not a simple rectangle. Besides the core 404, the illustrated guiding mechanism 402 comprises a panhandle 414 at the superior side and at least one (two are shown) tine 416 at the inferior side. While generally in the art panhandles and tines are thought of as either stand-alone features (such as the tines on a fork or a panhandle on a pan), in the present disclosure the panhandle and the tines are depressions in the body of the splint 102.

The panhandle 414 and the tines 416 prevent saliva from being collected and trapped within the guiding mechanism 402. Trapped saliva provides a breeding ground for oral bacteria that can lead to a bad taste in the mouth, bad breath, and potentially infection and periodontal disease. The panhandle 414 and the tines 416 allow saliva to drain readily from the core 404. Also, when the splint 102 is washed following the use, with the panhandle 414 and the tines 416, water drains quickly and efficiently from the core 404, which reduces the potential for mold or bacterial growth, especially along the corners of the core 404.

FIG. 4B shows the embodiment of FIG. 4A with the guided fin 104 nestled in the guiding mechanism 402. In these embodiments, the guided fin 104 comprises a guide rail 418, which is attached to the splint side of the guided fin 104. The guide rail 418 comprises a superior edge 420 and an inferior edge 422. The width of the guide rail 418 (in the direction parallel to the vertical axis) is such that the superior edge 420 abuts the superior wall 410 while the inferior edge 422 abuts the inferior wall 412 (shown in FIG. 4A). Consequently, the placement of the guide rail 418 within the core 404 causes the guide rail 418 to travel in only one direction, i.e., along the anteroposterior axis.

Figure 5:
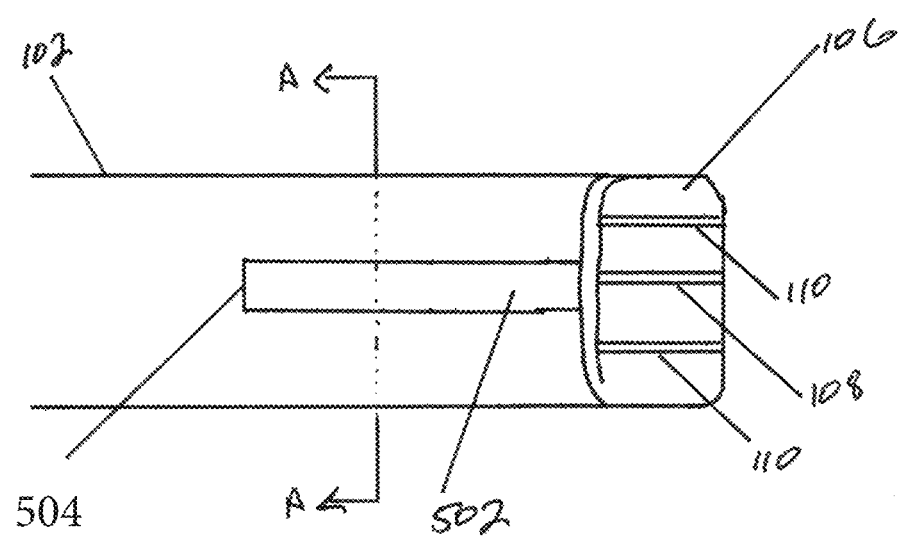
FIG. 5 is a side view of one embodiment of a channel of an embodiment of the adjustable fin location.

FIG. 5 illustrates another embodiment of the guiding mechanism 502 contemplated herein. In these embodiments, the guiding mechanism 502 is a rail or a groove that runs along the anteroposterior axis at the side of the splint 102. In some embodiments, the guiding mechanism 502 comprises a positive stop 504 at the anterior terminus of the guiding mechanism 502.

FIGS. 6A & 7A illustrate the cross-section of two separate embodiments of the guiding mechanism 502 along the A-A line. Referring now to FIG. 6A, the guiding mechanism 502 comprises a guide groove 612 cut along the side of the splint 102. The guide groove 612 forms a superior wall 604 and an inferior wall 606. In some embodiments, the walls 604 & 606 are parallel to the transverse plane. In other embodiments, such as the one shown in FIG. 6A, the walls 604 & 606 are at an angle with respect to the transverse plane. FIG. 6B illustrates an embodiment of a cross-section of the guided fin 104 that is compatible with the guiding mechanism 502 of FIG. 6A. The guided fin 104 comprises a guide rail 602, which has a superior edge 608, which is parallel to the wall 604, and an inferior edge 610, which is parallel to the wall 606. The shape of the guide rail 602 is such that it fits snugly within the guide groove 612.

The arrangement of the guiding mechanism 502 in the embodiment of FIGS. 7A & 7B is the mirror image of the guiding mechanism 502 of the embodiment of FIGS. 6A & 6B. In the case of FIGS. 7A & 7B, the guide rail 712 is on the splint 102 and the guide groove 702 is on the guided fin 104. The following features correspond to each other: wall 708 to wall 604; wall 710 to wall 606; edge 704 to edge 608; and edge 706 to edge 610.

In the embodiments where the walls 604,610,708,710 are not parallel to the transverse plane, the guided fin 104 is prevented from moving along the vertical or transverse axes due to the locking of the guide rail 602 inside the guide groove 612 (FIGS. 6A & 6B) or the guide rail 712 inside the guide groove 702 (FIGS. 7A & 7B).

In some embodiments, the splint 102 comprises two or more guiding mechanisms for the guided fin 104.

The embodiments shown in FIGS. 6A, 6B, 7A, & 7B illustrate an arrangement of the stabilizing rods 110 and the threaded rod 108. In these embodiments, the rods 110 & 108 are shown to be on a line. In some embodiments, the threaded rod 108 is placed offset from the line formed by location of the stabilizing rods 110.

In some embodiments, the guiding mechanisms disclosed herein comprise a positive stop. In these embodiments, when the guided fin 104 reaches the positive stop, the guided fin 104 does not advance anteriorly any further. The positive stop ensures that the guided fin 104 remains connected to the guiding mechanism and does not become disconnected if the threaded rod 108 is accidentally turned too many times. In some embodiments, the positive stop is in the form of a bump on, or the closure of, at the anterior end of the guide channel 202. In other embodiments, the threading on the threaded rod 108 ends so that it does not turn any further. Other mechanisms that prevent the guided fin 104 from jumping the guiding mechanism can be used.

In some embodiments, the threaded rod 108 has a driver grip. The driver grip allows for a tool to connect with the threaded rod 108 so a user can turn the rod 108. In some embodiments, the cross section of the driver grip resembles the cross section of the tool. For example: for a flat head screw driver as the tool, the driver grip is a linear slit on the end of the threaded rod 108; for a Phillips head screwdriver as the tool, the driver grip is shaped like a +; for an Allen wrench (hex key), the driver grip is a hexagonal dip; and the like.

In some embodiments, the driver grip is located at the posterior end of the threaded rod 108. In some of the currently available MADs, a threaded rod is turned by inserting a pin into a hole on the rod and moving the pin in the desired direction, orthogonal to the length of the pin. In these situations, to affect a full turn of the rod, the user must repeat the insertion-rotation act multiple, e.g., three, times. There are significant reports of user error in adjusting the fin location using the available methods because users become distracted and forget the number of times they have turned the rod. Having the driver grip at the posterior, or alternatively the anterior, end of the threaded rod 108 allows the users to affect a full turn without disengaging the tool from the driver grip.

In some embodiments, it is desirable for the user to change the distance D by an integer multiple of a given increment. In other words, $$D2=na+D1$$

where D1 and D2 are as defined above and in FIG. 2A, n is an integer, and a is a distance increment. In some embodiments, a is between about 0.1 to about 1 mm, for example, about 0.1, 0.5, or 1 mm, or other increments.

By "about" a certain value or "substantially" a certain value it is meant that the stated value comprises the range of values within ±25%, ±20%, ±10%, or ±5% of the stated value. Thus, by way of example only, if a distance is given as "about 5 mm," the range of distances between 3.75 mm (5 −25%) to 6.25 mm (5+25%) is envisioned. Likewise, when two values are said to be "substantially the same" it is meant that the values are within ±25%, ±20%, ±10%, or ±5% of each other.

In some embodiments, a full turn of the driver grip causes a one increment of displacement for the guided fin 104 along the guiding mechanism. For example, a full turn can cause a change in distance from D1 to D2 (see FIG. 2A) for an increment of between about 0.1 to about 1 mm.

In some embodiments, once the turning of the threaded rod 108 has caused a one increment change in distance D (FIG. 1), an audible or otherwise felt click notifies the user. In other embodiments, for example that shown in FIG. 1, the splint 102 further comprises a plurality of fiducial marks 112 on the splint 102 indicating the distance between the guided fin 104 and the back post 106.

The arrangement of the various features of the presently disclosed MADs is described above such that the guided fin 104 is connected to the upper splint 102 and the stationary fin 152 is connected to the lower splint 150. The ordinary artisan readily recognizes that the disclosed arrangement could be reversed. That is, in some embodiments, the guided fin 104 is connected to the lower splint 150 and the stationary fin 152 is connected to the upper splint 102.

As described in the U.S Patent Application Publication 2016/0184129, multiple splints having a stationary fin 152 can be prepared, where the stationary fin 152 in each of the splints is placed at a different distance from the back of the splint, while the splints are otherwise identical. The combination of multiple either lower or upper splints with a stationary fin with a corresponding splint (i.e., the other of the lower or upper splint) having a guided fin allows for a greater range of mandibular advancement, both in terms of the extent of the advancement and the number of increments within each unit of distance. Further, the mechanism allows for the above greater range to be obtained with fewer splints.

The presently disclosed mechanism allows for a more efficacious, more comfortable, and less expensive MAD for the patient.

What is claimed is:

1. A splint for a mandibular advancement device, the splint comprising:
   one or more guided fins, wherein each guided fin is located at a distance D from the back of the splint;
   a back post;
   at least one threaded rod connecting the back post to the guided fin,
      wherein the distance between the guided fin and the back post is changed when the threaded rod is turned either clockwise or counterclockwise; and
   a guiding mechanism;
   wherein the guiding mechanism comprises a guiding channel, wherein the guiding channel is an indentation in the body of the splint, and wherein the guiding channel comprises:
   a substantially rectangular core section, being at least partially bound by a posterior wall, an anterior wall, a superior wall, and an inferior wall;
   a panhandle at the superior wall; and
   at least one tine at the inferior wall.

2. The splint of claim 1, wherein the splint is an upper splint or a lower splint.

3. The splint of claim 1, wherein a gap between the guided fin and the splint at the posterior-most position of the guided fin is substantially the same width as the gap between the guided fin and the splint at the anterior-most position of the guided fin.

4. The splint of claim 1, wherein the guiding mechanism comprises a positive stop at the anterior end of the guiding mechanism.

5. The splint of claim 1, wherein the guiding mechanism further comprises at least one stabilizing rod connecting the back post to the guided fin.

6. The splint of claim 1, wherein the guided fin comprises a guide rail, attached to the splint side of the guided fin.

7. The splint of claim 6, wherein the guide rail comprises a superior edge and an inferior edge, wherein the superior edge of the guide rail abuts the superior wall of the core section, while the inferior edge of the guide rail abuts the inferior wall of the core section.

8. The splint of claim 1, wherein the guiding mechanism comprises:
   a guide groove cut along the side of the splint and a guide rail on the guided fin; or
   a guide rail on the splint and a guide groove cut along the side of the guided fin.

9. The splint of claim 8, wherein:
   the guide groove forms a superior wall and an inferior wall;
   the guide rail comprises a superior edge, which is parallel to the superior wall of the guide groove;
   the guide rail comprises an inferior edge, which is parallel to the inferior wall of the guide groove.

10. The splint of claim 9, wherein the superior edge and/or the inferior edge are at an angle with respect to the transverse plane.

11. An upper or a lower splint for a mandibular advancement device, the splint comprising:
   one or more guided fins, wherein each guided fin is located at a distance D from back of the splint;
   a back post;
   at least one threaded rod connecting the back post to the guided fin, wherein the distance between the one or more guided fins and the respective back post is changed when the threaded rod is turned either clockwise or counterclockwise;

at least one stabilizing rod connecting the back post to the guided fin;

a guiding mechanism, comprising:
  a positive stop at the anterior end of the guiding mechanism;
  a guiding channel, wherein the guiding channel is an indentation in the body of the splint, and the guiding channel comprises:
    a substantially rectangular core section, being at least partially bound by a posterior wall, an anterior wall, a superior wall, and an inferior wall;
    a panhandle at the superior wall; and
    at least one tine at the inferior wall; and
  the guided fin comprises a guide rail, attached to the splint side of the guided fin, wherein the guide rail comprises a superior edge and an inferior edge, wherein the superior edge of the guide rail abuts the superior wall of the core section, while the inferior edge of the guide rail abuts the inferior wall of the core section.

* * * * *